(12) United States Patent
Petit et al.

(10) Patent No.: US 11,559,821 B2
(45) Date of Patent: Jan. 24, 2023

(54) METHOD FOR USING AN ASSEMBLY FOR DISPENSING A FLUID PRODUCT

(71) Applicant: APTAR FRANCE SAS, Le Neubourg (FR)

(72) Inventors: Ludovic Petit, Vitot (FR); Olivier Martins, Les Damps (FR)

(73) Assignee: APTAR FRANCE SAS, Le Neubourg (FR)

( * ) Notice: Subject to any disclaimer, the term of this patent is extended or adjusted under 35 U.S.C. 154(b) by 0 days.

(21) Appl. No.: 15/103,959

(22) PCT Filed: Jan. 9, 2015

(86) PCT No.: PCT/FR2015/050050
§ 371 (c)(1),
(2) Date: Jun. 13, 2016

(87) PCT Pub. No.: WO2015/104511
PCT Pub. Date: Jul. 16, 2015

(65) Prior Publication Data
US 2016/0318051 A1 Nov. 3, 2016

(30) Foreign Application Priority Data

Jan. 13, 2014 (FR) ...................... 1450251

(51) Int. Cl.
*B05B 11/02* (2006.01)
*A61J 1/20* (2006.01)
(Continued)

(52) U.S. Cl.
CPC ............. *B05B 11/02* (2013.01); *A61J 1/2096* (2013.01); *A61M 5/3156* (2013.01);
(Continued)

(58) Field of Classification Search
CPC . B05B 11/02; B05B 11/0008; B05B 11/0035; B05B 11/0097; B05B 11/025;
(Continued)

(56) References Cited

U.S. PATENT DOCUMENTS 3,874,380 A * 4/1975 Baum ............... A61M 15/0028
128/200.14
3,874,381 A * 4/1975 Baum ..................... A61M 3/00
128/200.14

(Continued)

FOREIGN PATENT DOCUMENTS

| EP | 2 213 322 A1 | 8/2010 |
| FR | 2 561 925 A3 | 10/1985 |
| JP | 3047521 U | 4/1998 |

OTHER PUBLICATIONS

International Search Report for PCT/FR2015/050050 dated Apr. 10, 2015 [PCT/ISA/210].

(Continued)

*Primary Examiner* — Tuongminh N Pham
*Assistant Examiner* — Juan C Barrera
(74) *Attorney, Agent, or Firm* — Sughrue Mion, PLLC

(57) ABSTRACT

A method of using a fluid dispenser unit having a reservoir and a piston that slides in the reservoir. The unit includes an extractor head secured to the reservoir to suck fluid to be dispensed into the reservoir, and a spray head assembled on the extractor head to spray the fluid out from the reservoir. The method includes the steps of sucking a fluid to be dispensed into the reservoir through the extractor head; assembling the spray head on the extractor head; and spraying the fluid through the spray head. The step of sucking up a fluid to be dispensed includes a first step of extracting a fluid, such as a solvent, from an extraction reservoir, and a second step of mixing the fluid with a first substance, such (Continued)

as a powder or a lyophilisate, so as to form the fluid to be dispensed.

17 Claims, 3 Drawing Sheets

(51) Int. Cl.
*B05B 11/00* (2006.01)
*A61M 11/00* (2006.01)
*B05B 1/34* (2006.01)
*A61M 5/315* (2006.01)
*A61M 15/08* (2006.01)
*A61M 15/00* (2006.01)

(52) U.S. Cl.
CPC ............ *A61M 11/007* (2014.02); *B05B 1/341* (2013.01); *B05B 11/0008* (2013.01); *B05B 11/0035* (2013.01); *B05B 11/0097* (2013.01); *B05B 11/025* (2013.01); *B05B 11/3038* (2013.01); *A61M 15/0003* (2014.02); *A61M 15/0036* (2014.02); *A61M 15/08* (2013.01)

(58) Field of Classification Search
CPC .. B05B 1/341; B05B 11/3038; A61M 35/003; A61M 11/007; A61M 11/06; A61M 15/0036; A61M 15/08; A61M 5/3156; A61M 15/0003; A61M 15/0028; A61M 2205/073; A61M 5/284; A61M 5/31596; A61M 2005/1787; A61M 3/00; A61M 3/005; A61M 5/2066; A61J 1/2096; A61J 1/2089; A61J 1/2093; A61J 7/0053; A61J 1/2031; A61J 1/2072; A61J 1/201; A61J 1/2048; B65B 3/003
USPC ........................................................... 239/10
See application file for complete search history.

(56) References Cited

U.S. PATENT DOCUMENTS

| | | | |
|---|---|---|---|
| 4,767,416 A | 8/1988 | Wolf et al. | |
| 4,962,868 A * | 10/1990 | Borchard | A61M 11/06 128/200.14 |
| 5,125,892 A * | 6/1992 | Drudik | A61M 5/31596 604/200 |
| 5,961,489 A | 10/1999 | Hirota | |
| 6,349,850 B1 * | 2/2002 | Cheikh | A61J 1/2089 141/100 |
| 8,276,581 B2 * | 10/2012 | Kawamura | A61M 11/00 128/200.14 |
| 2011/0106045 A1 * | 5/2011 | Reynolds | A61J 1/2096 604/413 |

OTHER PUBLICATIONS

International Preliminary Report on Patentability issued by the International Bureau in counterpart International Application No. PCT/FR2015/050050, dated Jul. 28, 2016.

* cited by examiner

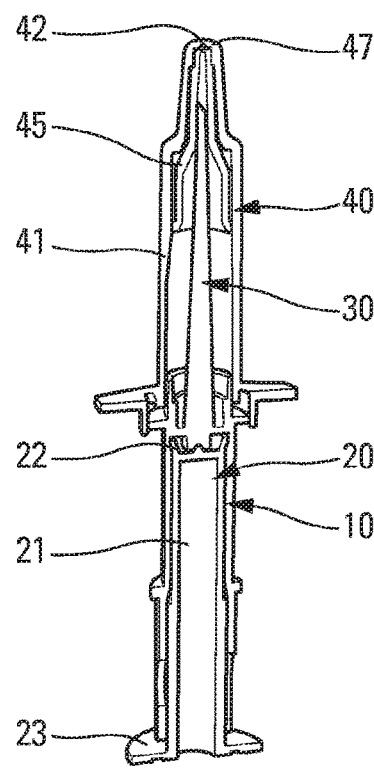 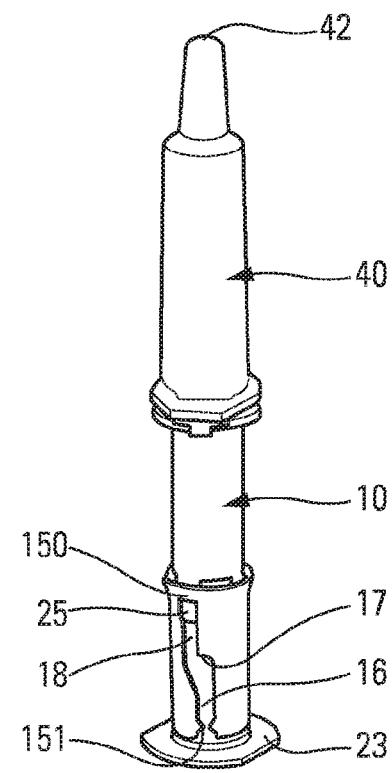 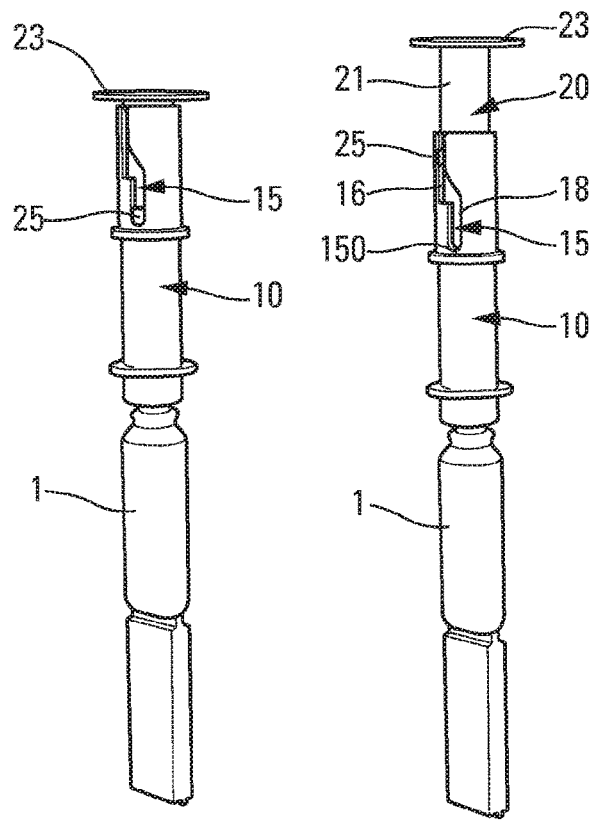 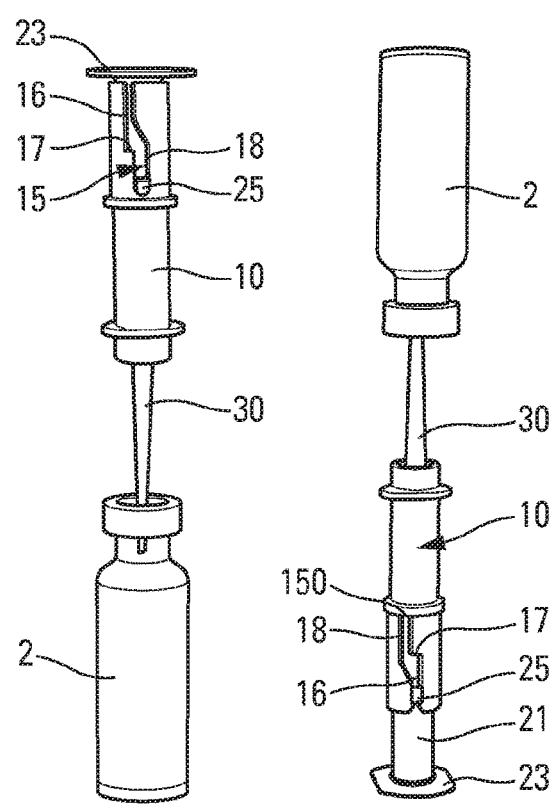
Fig. 1  Fig. 2  Fig. 3  Fig. 4  Fig. 5  Fig. 6

METHOD FOR USING AN ASSEMBLY FOR DISPENSING A FLUID PRODUCT

CROSS REFERENCE TO RELATED APPLICATIONS

This application is a National Stage of International Application No. PCT/FR2015/050050, filed on Jan. 9, 2015, which claims priority from French Patent Application No. 1450251, filed on Jan. 13, 2014, the contents of all of which are incorporated herein by reference in their entirety.

The present invention relates to a method of using a fluid dispenser unit, and such a unit for implementing said method.

Fluid dispenser devices are well known. They generally comprise a reservoir, dispenser means, and a dispenser head. The dispenser head may be a spray head, e.g. of the nasal type. Such spray heads generally comprise two parts, namely a body forming the head, and a part forming the nozzle, i.e. the portion that creates the spray by causing the fluid to swirl when it is dispensed. For an external nozzle, a small sleeve is engaged from the outside into the downstream end of the body so as to co-operate therewith to define said spray profile. For an internal nozzle, it is an insert inserted from the inside of the head that co-operates with the end wall of the body so as to define the spray profile. Either way, the spray profiles generally include a plurality of non-radial channels, in particular three, formed either in the end wall of the head, or in the sleeve forming the external nozzle, or in the insert forming the internal nozzle. Generally, spray heads are assembled on pump piston rods or valve members so as to guide the fluid that is dispensed from the pump or the valve towards the spray orifice. However, it has also been proposed to arrange a spray head directly on the outlet of a syringe-type reservoir so as to spray the content of said syringe rather than inject it through a needle. Document WO 00/71263 describes such an arrangement. Once again, such spray heads are still made with two or more parts that are assembled together. In particular, that implementation prevents such syringes being used in suction mode. In particular, a syringe with a spray head does not enable the suction mode that is typical of syringes, e.g. for sucking a fluid from an extraction reservoir. In addition, a syringe with a needle does not enable fluid to be sprayed while it is being dispensed.

Documents U.S. Pat. Nos. 5,961,489, 4,767,416, 3,874, 380, EP 2 213 322, FR 2 561 925 and U.S. Pat. No. 4,962,868 describe prior-art devices.

An object of the present invention is to provide a method of using a fluid dispenser unit that does not have the above-mentioned drawbacks.

Another object of the present invention is to provide a fluid dispenser unit that implements such a method, that is simple and inexpensive to manufacture and to assemble, and that can function both in suction mode and in expulsion mode.

Another object of the present invention is to provide such a method and such a fluid dispenser unit that make it possible to create a correct and reproducible spray.

The present invention thus provides a method of using a fluid dispenser unit comprising a reservoir for containing a fluid, and a piston that slides in said reservoir, said unit further comprising an extractor head that is secured to said reservoir so as to suck a fluid to be dispensed into said reservoir, and a spray head that is assembled on said extractor head so as to spray said fluid to be dispensed out from said reservoir, said method comprising the following steps: sucking a fluid to be dispensed into said reservoir through said extractor head; assembling said spray head on said extractor head; and spraying said fluid to be dispensed through said spray head.

Advantageously, said second step of mixing comprises: injecting said fluid, such as a solvent, into a mixing reservoir containing said first substance, so that said first substance and said fluid mix together in said mixing reservoir so as to form the fluid to be dispensed; then sucking said fluid to be dispensed into said reservoir through said extractor head.

Advantageously, in order to make it possible to evacuate the increased pressure generated in said mixing reservoir by injecting said fluid, said reservoir and said piston co-operate in non-airtight manner in the fully depressed position of the piston, so as to connect the inside of the mixing reservoir to the atmosphere in this fully depressed position of the piston.

The present invention also provides a fluid dispenser unit for implementing the above-mentioned method, said extractor head being made as a single piece integrally with said reservoir, in particular by molding a plastics material.

Advantageously, said extractor head includes an extractor needle.

Advantageously, said spray head includes a central expulsion channel that, in the flow direction of the fluid during spraying, is terminated by a spray orifice, a spray profile being provided upstream of said spray orifice.

Advantageously, said reservoir and/or said piston include(s) dose-fractioning means for dividing the fluid for dispensing that is contained in said reservoir into at least two doses for being sprayed during a plurality of successive actuations of said unit.

Advantageously, said dose-fractioning means comprise a lug of said piston that slides in a groove of said reservoir, said groove including a shoulder for blocking said lug after the first dose of fluid has been sprayed.

Advantageously, said reservoir and/or said piston include(s) energy accumulation means that require at least a predetermined force to be applied in order to make it possible to spray said fluid to be dispensed.

Advantageously, said energy accumulation means comprise at least one projection that co-operates with said lug of said piston, said lug being able to pass beyond said energy accumulation means when at least said predetermined force is applied on said piston.

These advantages and characteristics and others of the present invention appear more clearly from the following detailed description, given by way of non-limiting example, and with reference to the accompanying drawings, and in which:

FIG. 1 is a diagrammatic section view of a dispenser unit in a first advantageous variant embodiment of the present invention, with the spray head in its assembled position;

FIG. 2 is a diagrammatic side view of the dispenser unit shown in FIG. 1;

FIGS. 3 and 4 are diagrammatic views of the dispenser unit in FIGS. 1 and 2 with the spray head in its non-assembled position, during a stage of extracting a fluid such as a solvent from an extraction reservoir;

FIGS. 5 and 6 are diagrammatic views similar to the views in FIGS. 3 and 4, during stages of injecting fluid such as a solvent into a mixing reservoir, and of sucking the fluid to be dispensed from said mixing reservoir;

Figure 7:
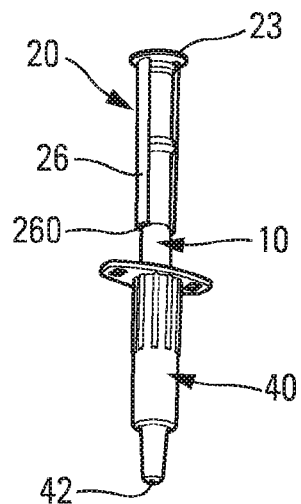
Figure 8:
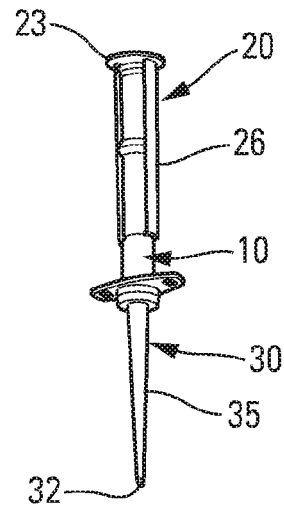
Figure 9:
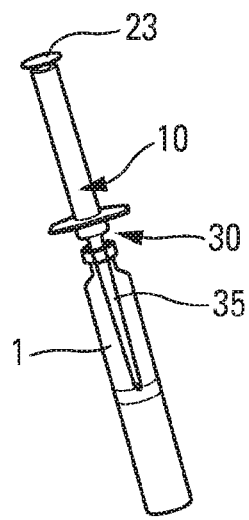
Figure 10:
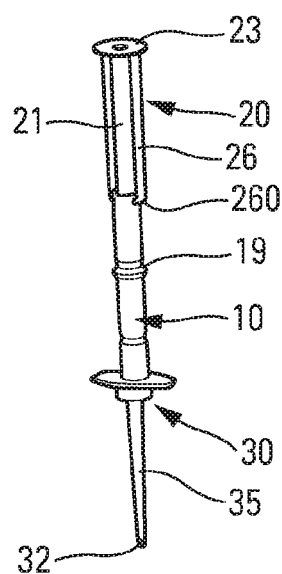
Figure 11:
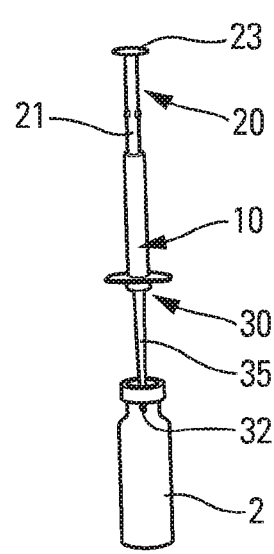
Figure 12:
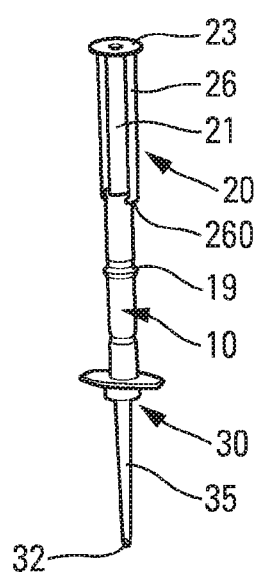
Figure 13:
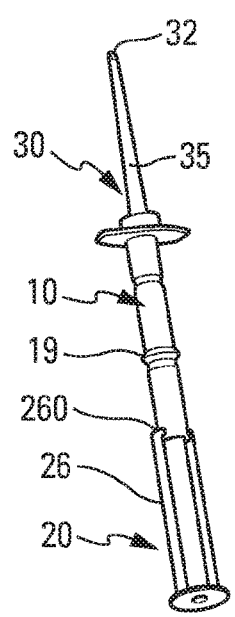
Figure 14:
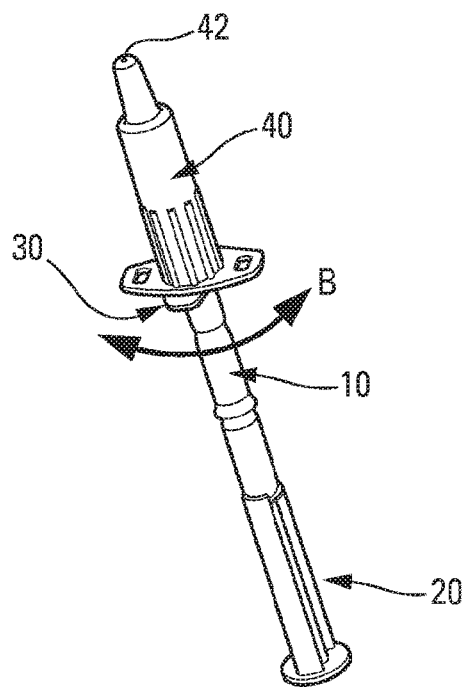
Figure 15:
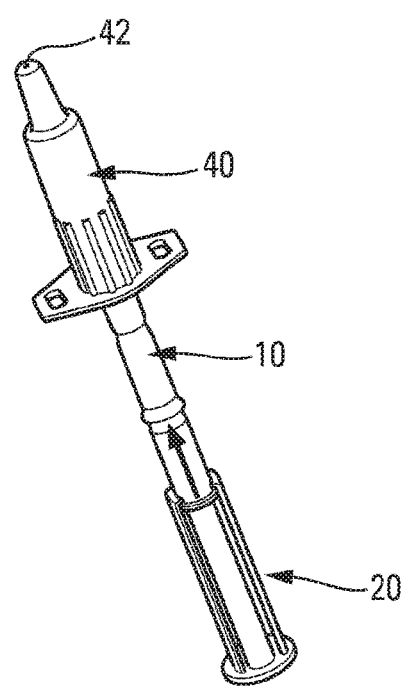
Figure 16:
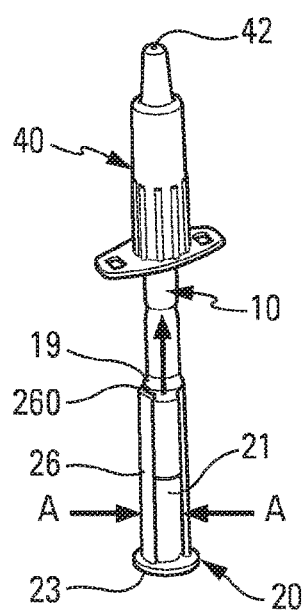
Figure 17:
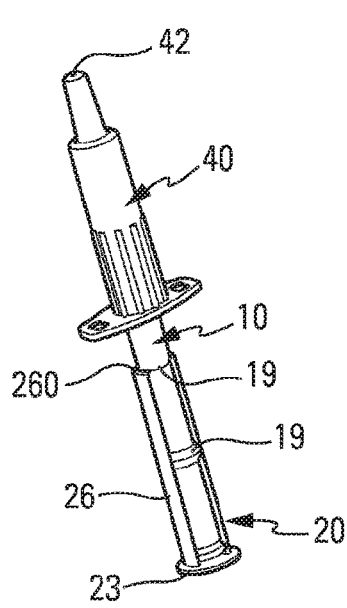
Figure 18:
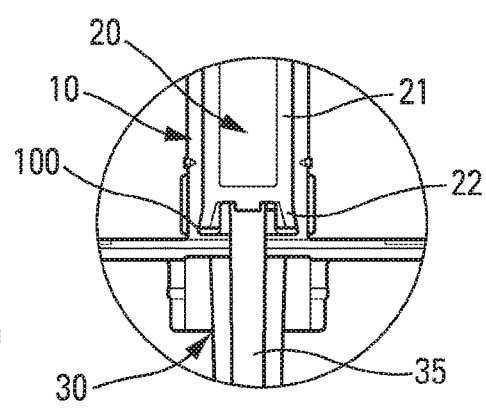

FIGS. 7 to 17 show, in very diagrammatic manner, a method of using a dispenser unit in a second advantageous variant embodiment of the present invention, FIG. 9 showing a stage of extracting solvent from an extraction reservoir, FIG. 11 showing a stage of injecting the solvent into a mixing reservoir, FIG. 12 showing the dispenser unit containing the fluid to be dispensed, FIGS. 13 and 14 showing the spray head being assembled on the extractor head, and FIGS. 15 to 17 showing the spraying of two half-doses of fluid to be dispensed; and FIG. 18 is a diagrammatic view of a detail of the mixing reservoir being vented at the end of the solvent-injection stage.

FIGS. 1 to 6 show a dispenser unit in a first advantageous variant embodiment of the invention. The dispenser unit comprises: a reservoir 10 of the syringe type; a piston 20 that slides in said reservoir between a retracted position and a depressed position; an extractor head 30 that is secured to said reservoir 10, in particular that is made integrally therewith; and a spray head 40 that comes to be assembled on said extractor head. FIGS. 1 and 2 show the spray head in its assembled position, and in FIGS. 3 to 6 the spray head is not in its assembled position.

The reservoir 10 and the extractor head 30 are preferably made by molding a plastics material.

The piston 20 comprises a piston element 22 that is secured to an actuator rod 21 that is actuated by the user at the moment of dispensing, in particular by pressing manually on an end collar 23 of the piston rod 21. The piston element 22 may be made as a single piece integrally with the piston rod 21, e.g. by molding a plastics material, or it may form a separate element that is fastened to said piston rod, e.g. overmolded thereon. In this configuration, the piston element 22 may be made out of a material that is different from the material of the piston rod 21.

In the variant in FIGS. 1 to 6, the reservoir 10 includes at least one groove 15, 16 that co-operates with a lug 25 of said piston rod 21. The lug 25 projects radially outwards and slides in said at least one groove 15 while said dispenser unit is being actuated. Advantageously, the groove 15 includes firstly a final abutment 150 that co-operates with said lug 25 so as to define the depressed position of the piston 20, and secondly at least one lateral projection 151 that co-operates with said lug 25 so as to define the retracted position of the piston 20.

The groove 15 may include a shoulder 17 that forms dose-fractioning means. Thus, while the piston 20 is being actuated with a view to spraying the fluid to be dispensed, the lug 25 of the piston 20 slides axially in a first groove portion 16, and the lug 25 is stopped by said shoulder 17 of the groove 15. This defines the first dose by interrupting the actuation stroke of the piston 20 in the reservoir 10. By way of example, the user should then turn the piston 20 a little, so as to bring the lug 25 to face a second groove portion 18 so as to be able to spray the second dose. Naturally, the invention also applies to a single-dose device in which all of the fluid to be dispensed is sprayed in a single dose. It may also apply to devices that contain more than two doses, e.g. three or four doses.

Advantageously, the groove 15 includes energy accumulation means, e.g. such as projections, that may co-operate with the lug 25 at the start of each actuation stroke so as to constrain the user to exert a force on the piston 20 that is at least sufficient to overcome the resistance generated by said energy accumulation means. When this force is achieved, the lug 25 passes beyond said energy accumulation means, and this suddenly releases the energy accumulated in the user's hand, thereby guaranteeing that the actuation stroke, or the half-actuation stroke in the two-dose embodiment shown, is achieved in full. Naturally, the energy accumulation means may be made in any appropriate way, and the above-described projections are only an advantageous embodiment. For example, it is possible to envisage constrictions or breakable bridges in said groove 15.

In the variant in FIGS. 7 to 17 which show a second advantageous variant embodiment of the invention, the dose-fractioning means are different. In this embodiment, they comprise a slotted outer sleeve 26 of the piston 20, said slotted sleeve 26 extending around said reservoir 10. On its radially-outer cylindrical surface, the reservoir 10 includes at least one shoulder 19 that co-operates with the axial end edge 260 of said slotted sleeve 26 so as to stop the actuation stroke of the piston 20 after spraying the first dose. This is shown in FIG. 16. To enable the continuation of the actuation stroke of the piston 20, the user must pinch the slotted sleeve 26 of the piston 20 laterally in the direction of arrows A in FIG. 16, and this moves the axial end edge 260 of said slotted sleeve 26 radially apart a little, thereby unblocking the piston 20 from the shoulder 19 of the reservoir, and thereby making it possible to spray the second dose of fluid.

Other variants may be envisaged for the dose-fractioning means, e.g. an elastically-deformable portion that is formed either on the piston or on the reservoir, and that deforms when sufficient force is applied on the piston. In this configuration, the dose-fractioning means could simultaneously form energy accumulation means. Other variants may also be envisaged.

The extractor head 30 supports a needle 35 that is provided with an orifice 32. The needle 35 is thus advantageously made as a single piece integrally with said reservoir 10, e.g. by molding a plastics material. In a variant, the needle may be fastened to the reservoir in any appropriate way, e.g. by overmolding. In this configuration, the needle may be made out of a different material, e.g. metal.

The spray head 40 comprises a hollow body 41 that is provided with an end wall 47 that includes a spray orifice 42. Advantageously, the hollow body 41 contains an insert 45 upstream from the spray orifice 42 for fitting on the extractor head 30. The insert 45 advantageously includes one or more lateral passages (not shown) that enable the fluid to pass from the inside of said insert 45 to the outside. The axial end wall of said insert 45 is thus closed, and the outside surface of said end wall of said insert may co-operate with the end wall 47 of the spray head 40 to form a spray profile, e.g. comprising swirl channels and a spray chamber. The spray profile makes it possible to create a good spray while the fluid is being dispensed through said spray head 40. The spray profile may be formed on the outside surface of said end wall of said insert. In a variant, the spray profile may be provided in the end wall 47 of said spray head, in which configuration the outside surface of the axial end wall of the insert could be smooth. Preferably, each of said spray head 40 and of said insert 45 are made by molding a plastics material.

FIGS. 3 to 6 show some of the stages of the method of using a dispenser unit in the first variant embodiment of the present invention. FIGS. 7 to 17 show all of the stages of using the dispenser unit in the second variant embodiment of the invention. The various stages of use are identical in the two embodiments, only the structures of the piston 20 and of the reservoir 10 differ, as explained above.

Thus, FIGS. 3 and 4 firstly and FIG. 9 secondly show the extraction stage, with the needle 35 of the extractor head 30 inserted into an extraction reservoir 1 containing a fluid to be sucked into the reservoir 10, in particular a solvent such as water. Extraction is performed in conventional manner by causing the piston 20 to slide in the reservoir 10 away from said needle 35, thereby sucking the fluid from said extraction reservoir 1 into said reservoir 10.

FIG. 5 firstly and FIG. 11 secondly show said fluid, which has been extracted beforehand from said extraction reservoir 1, being injected into a mixing reservoir 2 that contains another substance, typically an active ingredient, in particular in the form of a powder or of a lyophilisate. Mixing the powder with the solvent makes it possible to reconstitute the fluid to be dispensed in said mixing reservoir 2. Advantageously, the mixing reservoir 2 may be stirred or shaken so as to encourage said mixing. Advantageously, in order to make it possible to evacuate the increased pressure generated in the mixing reservoir 2 by injecting the solvent, the reservoir 10 and the piston 20 are made so that they do not co-operate in airtight manner in the fully depressed position of the piston 20, as can be seen in FIG. 18, which shows a radial gap 100 in the end wall of the reservoir 10. This makes it possible to connect the inside of the mixing reservoir 2 to the atmosphere via the needle 35 and said air passage created between the piston 20 and the reservoir 10 in the depressed position of the piston 20. This thus makes it possible to avoid any risk of incomplete reconstitution in the mixing reservoir 2, which could occur if the pressure in said mixing reservoir were increased.

After reconstitution, the fluid to be dispensed is sucked once more into the reservoir 10 through the needle 35 of the extractor head, as shown diagrammatically in FIG. 6.

The spray head 40 is then assembled around said extractor head 30, and the fluid to be dispensed may then be sprayed through said spray head 40. Advantageously, the spray head 40 is clipped or snap-fastened on the reservoir 10 and/or on the extractor head 30, e.g. by turning through one fourth of a turn as shown by arrow B in FIG. 14. During this assembly, the orifice 32 of the needle 35 comes to co-operate in substantially leaktight manner in said insert 45 of said spray head 40. Advantageously, provision may be made for assembly of the spray head 40 to be made inseparable, so as to avoid reusing the dispenser unit. In addition, the spray head 40 could be pre-assembled in removable manner on said extractor head 30 prior to use, the user thus being able to remove said spray head 40, as shown in FIGS. 7 and 8, so as to perform the extraction, injection, and suction stages of the reconstituted mixture, and then return it into its assembled position so as to perform spraying. In a variant, the dispenser unit could be provided with the spray head 40 unassembled prior to use.

In another variant of the invention, the dispenser unit of the invention could be used for sucking the fluid to be dispensed directly from a source reservoir, without there being the stages of extracting fluid, such as a solvent, from an extraction reservoir, then of injecting the fluid into a mixing reservoir.

In addition, the reservoir 10 of the dispenser unit could contain a first substance, e.g. a power or a lyophilisate, and the fluid, such as a solvent, sucked from the extraction reservoir 1 is then mixed with said first substance directly in said reservoir 10 during the extraction stage, without it being necessary to pass via a mixing reservoir.

In another variant, a plurality of different fluids may be sucked from a plurality of different extraction reservoirs in order to be mixed in the reservoir 10 prior to spraying.

Although the present invention is described above with reference to various advantageous embodiments thereof, it is clear that any useful modification could be applied thereto by a person skilled in the art, without going beyond the ambit of the present invention, as defined by the accompanying claims.

The invention claimed is:

1. A method of using a fluid dispenser unit comprising a reservoir for containing a fluid, and a piston that slides in said reservoir, said unit further comprising an extractor head that is secured to said reservoir so as to suck a fluid to be dispensed into said reservoir, and a spray head that is assembled on said extractor head so as to spray said fluid to be dispensed out from said reservoir, said method comprising the following steps:
   sucking a fluid to be dispensed into said reservoir through said extractor head;
   assembling said spray head on said extractor head; and
   spraying said fluid to be dispensed through said spray head;
   wherein said step of sucking up a fluid to be dispensed comprises a first step of extracting a fluid from an extraction reservoir, and a second step of mixing said fluid with a first substance so as to form said fluid to be dispensed; and
   wherein said extractor head includes an extractor needle that is inserted at least in part into the extraction reservoir so that at least a tip of the extractor needle is inserted into and directly contacts the fluid in the extraction reservoir on an outer and an inner surface of the tip during the first step of extracting the fluid and through which the fluid is extracted from the extraction reservoir;
   wherein said extractor head, said extractor needle and said reservoir are molded in one single piece to form an integral one-piece construction that is maintained during the sucking and spraying steps;
   wherein, during the spraying step of the fluid to be dispensed through said spray head, said fluid to be dispensed flows out from the reservoir through said extractor needle and through said spray head; and
   wherein a spray direction of the spray head corresponds to a longitudinal axis of the extractor needle.

2. A method according to claim 1, wherein said second step of mixing comprises: injecting said fluid into a mixing reservoir containing said first substance, so that said first substance and said fluid mix together in said mixing reservoir so as to form the fluid to be dispensed; then sucking said fluid to be dispensed into said reservoir through said extractor head.

3. A method according to claim 2, wherein, in order to evacuate increased pressure generated in said mixing reservoir by injecting said fluid, said reservoir and said piston co-operate in non-airtight manner in a fully depressed position of the piston, so as to connect the inside of the mixing reservoir to the atmosphere in the fully depressed position of the piston.

4. The method according to claim 2, wherein said fluid is a solvent.

5. The method according to claim 1, wherein said spray head includes a central expulsion channel that, in a flow direction of the fluid during spraying, is terminated by a spray orifice, a spray profile being provided upstream of said spray orifice.

6. The method according to claim 1, wherein said reservoir and/or said piston include(s) dose-fractioning means for dividing the fluid for dispensing that is contained in said reservoir into at least two doses for being sprayed during a plurality of successive actuations of said unit.

7. The method according to claim 6, wherein said dose-fractioning means comprise a lug of said piston that slides in a groove of said reservoir, said groove including a shoulder for blocking said lug after the first dose of fluid has been sprayed.

8. The method according to claim 7, wherein at least one of said reservoir or said piston includes energy accumulation means and wherein said energy accumulation means comprise at least one projection that co-operates with said lug of said piston, said lug being able to pass beyond said energy accumulation means when at least said predetermined force is applied on said piston.

9. The method according to claim 1, wherein said reservoir and/or said piston include(s) energy accumulation means that require at least a predetermined force to be applied in order to spray said fluid to be dispensed.

10. The method according to claim 1, wherein said integral construction is a one-piece integral construction comprising said extractor head, said extractor needle and said reservoir.

11. The method according to claim 10, wherein said one-piece integral construction comprising said extractor head, said extractor needle and said reservoir is formed by molding a plastics material.

12. The method according to claim 1, wherein said first substance is a powder or a lyophilisate.

13. The method according to claim 1, wherein the fluid that is extracted from the extraction reservoir is a solvent.

14. The method according to claim 1, wherein the extractor needle directly contacts the fluid in the extraction reservoir when inserted at least in part into the extraction reservoir during the first step of extracting the fluid.

15. The method according to claim 1, wherein the extractor head, the extractor needle and the reservoir are in a fixed configuration that is maintained during the sucking and spraying steps.

16. The method according to claim 1, wherein the tip of the extraction needle is beveled.

17. A method of using a fluid dispenser unit comprising a reservoir for containing a fluid, and a piston that slides in said reservoir, said unit further comprising an extractor head that is secured to said reservoir so as to suck a fluid to be dispensed into said reservoir, and a spray head that is assembled on said extractor head so as to spray said fluid to be dispensed out from said reservoir, said method comprising the following steps:

sucking a fluid to be dispensed into said reservoir through said extractor head;

assembling said spray head on said extractor head; and spraying said fluid to be dispensed through said spray head;

wherein said step of sucking up a fluid to be dispensed comprises a first step of extracting a fluid from an extraction reservoir, and a second step of mixing said fluid with a first substance so as to form said fluid to be dispensed; and wherein said extractor head includes an extractor needle that is inserted at least in part into the extraction reservoir so that at least a tip of the extractor needle is inserted into and directly contacts the fluid in the extraction reservoir on an outer and an inner surface of the tip during the first step of extracting the fluid and through which the fluid is extracted from the extraction reservoir;

wherein said extractor head, said extractor needle and said reservoir form an integral one-piece construction that is maintained during the sucking and spraying steps;

wherein, during the spraying step of the fluid to be dispensed through said spray head, said fluid to be dispensed flows out from the reservoir through said extractor needle and through said spray head; and wherein a spray direction of the spray head corresponds to a longitudinal axis of the extractor needle.

\* \* \* \* \*